United States Patent [19]
Greenspan et al.

[11] Patent Number: 5,834,008
[45] Date of Patent: Nov. 10, 1998

[54] COMPOSITION AND METHOD FOR ACCELERATION OF WOUND AND BURN HEALING

[75] Inventors: David C. Greenspan; Jon K. West, both of Gainesville, Fla.

[73] Assignee: U.S. Biomaterials Corp., Alachua, Fla.

[21] Appl. No.: 715,911

[22] Filed: Sep. 19, 1996

[51] Int. Cl.$^6$ ..................................................... A61F 13/02
[52] U.S. Cl. ........................................... 424/443; 424/449
[58] Field of Search ..................................... 424/443, 447

[56] References Cited

U.S. PATENT DOCUMENTS

| | | | |
|---|---|---|---|
| 4,103,002 | 7/1978 | Hench | 428/155 |
| 5,000,746 | 3/1991 | Meiss | 604/304 |
| 5,352,715 | 10/1994 | Wallace | 523/115 |
| 5,501,706 | 3/1996 | Arenberg | 623/16 |
| 5,591,453 | 1/1997 | Ducheyne | 424/484 |

*Primary Examiner*—Thurman K. Page
*Assistant Examiner*—G. Brouillette
*Attorney, Agent, or Firm*—Burns, Doane, Swecker & Mathis, LLP

[57] ABSTRACT

A method for treating wounds including contacting a wound with an effective wound healing amount of bioactive glass and topical antibiotic and composition for the accelerated healing of wounds and burns including particulates of bioactive glass and at least one topical antibiotic.

12 Claims, 2 Drawing Sheets

COMPOSITION AND METHOD FOR ACCELERATION OF WOUND AND BURN HEALING

FIELD OF THE INVENTION

The present invention relates to a treatment composition and method for the accelerated healing of wounds and burns. More specifically, the present invention relates to the combination and use of particles of bioactive glass and one or more topical antibiotics. The present invention also relates to a treatment composition and method for the accelerated healing of wounds and burns including the combination of bioactive glass, one or more topical antibiotics and wound or burn dressings.

BACKGROUND OF THE INVENTION

When an injury occurs, cell damage comes from the precipitating event, such as a cut, resulting in ruptured cells and severed or crushed capillaries and other blood vessels. The interruption of blood flow produces anoxia, causing the death of additional cells. Within 15 minutes of injury the wound is filled with dead and dying cells, extracellular substances (collagen, elastic fibers, fat and ground substances), extravasated blood, and possibly bacteria and viruses introduced by the injurious agent. Tissue damage is not restricted to the initial area of injury. It may increase over the next several hours or days as a result of the release of lysomal enzymes from the injured cells or as a consequence of swelling and infection. (See Reese et al., Role of Fibronectin in Wound Healing, the subject matter of which is hereby incorporated by reference.

Coagulation, the first phase of the healing process, bridges the gap between the injury and the inflammatory response, the second phase of wound healing. It stops the loss of blood and restores some of the mechanical and physical integrity to the damaged tissue. The proteins of the coagulation cascade are normally confined to the intravascular space but are released into the tissues after blood vessel disruption. Coagulation is initiated by either the intrinsic or extrinsic pathway, both of which must be activated for maximum fibrin formation. The result of the activation of either of the two coagulation pathways is the generation of thrombin, which in turn catalyzes the conversion of fibrinogen to fibrin monomer. Fibrin monomer spontaneously polymerizes to form the clot. Just after polymerization, the fibrin fibers are held together by hydrophobic and ionic forces and are relatively unstable. Fibrin stabilizing factor, which is generated from its proenzyme by thrombin, covalently cross-links the fibrin fibrils by catalyzing a transamination reaction between glutamine and lysine residues in adjacent fibers. The cross-linking of fibers greatly increases the mechanical strength of the clot. Platelets, along with other blood cells, are trapped in the fibrin mesh as the clot forms by fibronectin. The platelet surfaces are heavily coated, and each looks like a nexus with the fibrin fibers radiating out from it.

The second phase of wound repair is the inflammatory response, which is necessary for subsequent phases of healing. It is initiated by the release of histamine and serotonin from platelets and mast cells and by kinins. Histamine and kinins act to increase capillary dilation, opening previously closed capillaries in the area of injury. The increased blood flow through the capillary beds produces two of the characteristics of the inflammatory response: redness and heat. Prostaglandin release within a few hours of injury results in the full development of the inflammatory response, which may last from 3 to 5 days depending on the extent of the injury. The extreme vasodilation produced by the factors just discussed causes a widening of the endothelial cell junctions lining the capillaries. Fluid and macromolecular components of blood escape into the tissues through the gaps, producing swelling, the third characteristic of the inflammatory response. If the swelling is extensive, it may interrupt blood flow, increasing the extent of injury as a result of anoxia . Pain, the final characteristic of inflammation, results form a combination of the kinins as well as the direct effect of lysosomal enzymes and pressure from the swelling on nerve endings.

Control of infection at the wound site is of critical importance in successful wound repair. Infections delay healing, enlarge the wound lesion, may lead to systemic infection, and greatly increase the likelihood of disfiguring and physically debilitating scars. Vasodilation of the capillary beds reduces the velocity of blood through the capillaries. This, along with the production of potent chemotactic factors from the complement fixation and the release of chemotactic agents from the damaged tissue, cause the accumulation of polymorphonuclear leukocytes ("PMN's") along the walls of the capillaries which are the host's major cellular defense against infection. The PMN's subsequently pass through the endothelial junctions of the capillary wall into the site of the injury. If bacteria are present in the wound, they may release soluble chemotactic factors and/or activate complement with the subsequent generation of chemotactic fragments. PMN's at the site of an infection or injury release substance that affect the PMNs' mobility, keeping them at the site. Fibronectin facilitates the attachment of the bacterium to the membrane of the phagocyte.

Dead cells, cellular debris, and extracellular proteins must then be removed or readsorbed to allow revascularization and repair to continue. Macrophages are primarily responsible for the clearance of wound debris. Wound macrophages, like wound PMN's are actively phagocytic. They migrate into the wound using the fibers of the fibrin clot as a scaffold to move within the clot, attaching to the fibers through fibronectin. The macrophages encounter, engulf, and destroy the dead cells trapped in the clot matrix, as well as the damaged cells from the wound margin. The fibrin clot itself is resolved primarily by the activation of the plasminogen that was incorporated into the fibers during their formation. Some of the fibrin fragments are engulfed by macrophages in the area. Since most of the clot fragments are released away from the area of the most intense macrophage activity, many of the fragments are removed by lymphatic drainage and thus enter the circulation. These soluble complexes are removed by the sessile cells of the RES, primarily those of the spleen and liver. Also, PMN's trapped in the clot die as a result of anoxia, releasing their lysosomal contents. These enzymes attack the surrounding clot and dissolve it. Although the release of lysosomal enzymes by PMN's may be considered beneficial to the host in most cases, they may also increase tissue destruction and delay healing. If the PMN's accumulate rapidly within the wound and remain there (as in an infection), their lysosomal enzymes dissolve significant portions of the clot, removing the framework used by the macrophages and fibroblasts to move into the wound and recolonize it. These areas of destruction must eventually be drained or slowly removed by the macrophages. The dissolved portion of the clot is then replaced as part of the chronic inflammatory response.

Repair, or fibroplasia, of the damaged tissue occurs during some of the above stages. Within 12 to 24 hours of injury, fibroblasts, including those at some distance from the wound margins, begin to move toward the area of injury and to proliferate. This response is apparently due to factors released by the injured tissue and platelets and possibly to factors released by the kinin, complement or coagulation cascades. The proliferating fibroblasts derive part of their nutrients from the components of tissue debris and cells released by macrophages. The fibroblast phase may last 2 to 4 weeks in a skin wound, whereas it may persist several months in an injury to the stomach or intestines. Fibroblasts, as the macrophages did, use the fibers of the fibrin clot as a scaffold to move into and within the damages area. The Fibroblasts synthesize and secrete sufficient quantities of fibronectin to promote their own attachment to fibronectin deficient substrates.

Angiogenesis, or revascularization, begins with the growth of capillary buds into the area directly behind the fibroblasts. In the early phases of wound repair, the capillaries are much more numerous than in normal tissue, which probably reflects the high oxygen and nutrient requirements of the rapidly regenerating tissue The capillaries are very leaky, which facilitates the movement of cells and macromolecule into the wound site. Eventually, the capillaries originating from one side of the wound grow into contact with capillaries originating from the other sides and fuse, reestablishing complete circulation within the wound.

By the end of the fifth day after the injury, fibroblasts begin laying down large quantities of collagen. The collagen molecule is synthesized on the membrane of the endoplastic reticulum. It then undergoes extensive postranslational modification, hydroxylation, glycosylation, and further steps —to form the procollagen molecule. The procollagen molecule is then secreted and is further modified to tropocollagen by specific serum peptidasees. These activated tropocollagen molecules quickly polymerize to form increasingly large collagen fibers. Thereafter, crosslinking among the collagen fibers occurs. The collagen network in effect replaces the fibrin clot as the major structural element of the wound. This becomes particularly important during the remodeling phase of wound healing.

Reepithelialization begins to occur within a few hours of injury as the attachment of the epithelial cells to the dermis loosened near the margin of the wound, and the cells begin to migrate over the defect, always maintaining contact with the mesenchymal tissue. By 48 hours after the injury, the cells are also beginning to proliferate to replace the lost cells. The epithelial cells continue to divide after the bridge is complete to form a thicker epithelium. Wound contracture aids reepithelialization insofar as it reduces the size of the defect to be reepithelialized by as much as 50%. Contracture is believed to occur as a result of the cellular element of the granulation tissue in the wound—the fibroblasts and myofibroblasts.

Remodeling is the last step of wound healing. Scar tissue continues to gain tensile strength for several months after collagen content stabilizes. This gain in strength comes from the rearrangement of the collagen in the wound and perhaps form increased crosslink of the collagen. Collagen accumulation is the sum of synthesis and destruction, and both occur simultaneously during the wound healing process. After about 14 days, a balance between collagen synthesis and degradation is reached. The collagenase involved in the remodeling comes from epithelial cells, from fibroblasts encountering new epithelium, and from macrophages that contain collagenase in their lysosomes.

Typical wound healing takes anywhere from 5 to 21 days. This time period is of course longer for the immune compromised patient because such patients are frequently unable to sufficiently stabilize the wound and ward off infection which prevents the proper adherence of fibrin, fibronectin or collagen at an acceptable rate at the locus of the wound. For example, those with vasculitis or other rheumatic or diabetic diseases frequently experience wound healing times far in excess of several weeks. Diabetics frequently develop lesions that take weeks to heal. Others, such as those with artificial limbs have continuous injury at the point of contact between the limb and the point of attachment to the body. Burns also present healing problems insofar as the burned tissue is incapable of timely production of fibrin. Accordingly, there is a great need to shorten the duration of time necessary for wound or burn healing to occur.

In an attempt to augment soft tissue, it has been previously suggested in U.S. Pat. No. 4,837,285 to fill and protect a wound with resorbable collagen matrix beads, the beads having an average pore size of from 50 to 350 microns, and the collagen comprising from 1 to 30% by volume of the beads. The collagen matrix is sufficiently open to stimulate cellular ingrowth therethrough and yet sufficiently stiff and non-compressible to fill and protect a wound. The formulation is also sufficiently moisture and gas permeable to prevent liquid pooling on a wound and to permit sufficient oxygen diffusion for promoting wound healing. This patent, however, fails to disclose any method for actually enhancing the rate of wound healing.

Accordingly, it is an object of the present invention to provide a composition and method capable of dramatically enhancing the time required for wound and burn healing.

It is further an object of the present invention to provide a composition and method capable of quickly stabilizing a wound or burn.

It is yet another object of the present invention to increase the likelihood that a skin graft will "take".

SUMMARY OF THE INVENTION

The present invention is directed to a method for treating wounds including contacting a wound with an effective wound healing amount of bioactive glass and topical antibiotic. The present invention is also directed to a composition for the accelerated healing of wounds and burns including particulates of bioactive glass and at least one topical antibiotic. The present invention is further directed to a method for grafting skin including applying bioactive glass to a graft and then placing the graft.

DETAILED DESCRIPTION OF THE PREFERRED EMBODIMENTS

Figure 1:
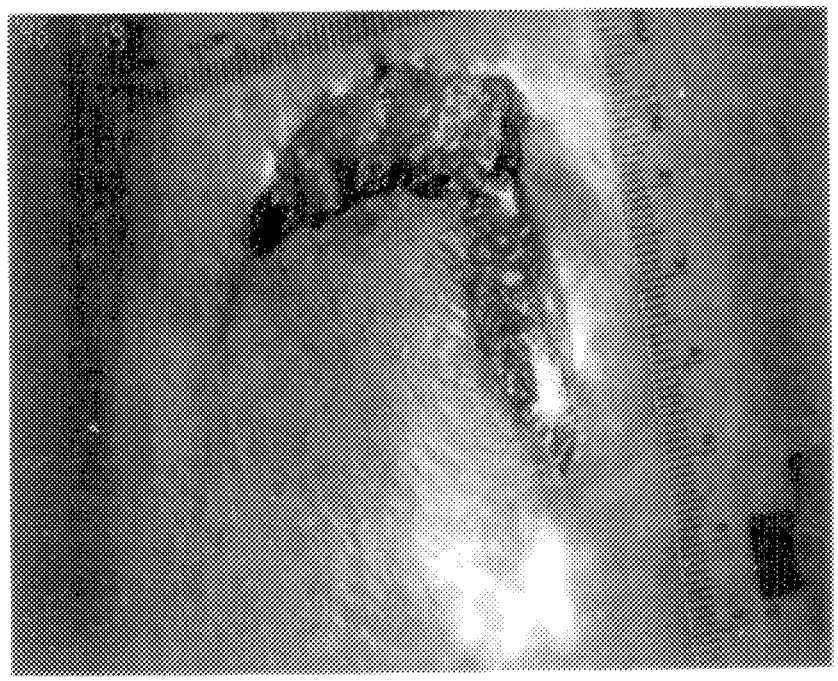
FIG. 1 is a photograph of a wound in patient with vasculitis taken soon after the wound was inflicted before treatment with a composition in accordance with the present invention.

It has unexpectedly been discovered that the combination of particulate bioactive glass and a topical antibiotic yields a composition which is capable of dramatically reducing the amount of time necessary for wound healing to occur.

Applicants have found that the combination of the present invention augments the natural healing process. The effect of the combination of the present invention is most dramatically illustrated in the immune compromised patient whose ability to heal wounds is somewhat suppressed.

Particulate bioactive glasses in accordance with the present invention typically have the following composition by weight percentage:

| | |
|---|---|
| $SiO_2$ | 40–60 |
| CaO | 10–30 |
| $Na_2O$ | 10–35 |
| $P_2O_5$ | 2–8 |
| $CaF_2$ | 0–25 |
| $B_2O_3$ | 0–10 |
| $K_2O$ | 0–8 |
| MgO | 0–5 |

The preferred composition of the bioactive glass is:

| | |
|---|---|
| $SiO_2$ | 45 |
| CaO | 24.5 |
| $Na_2O$ | 24.5 |
| $P_2O_5$ | 6 |

The preferred particle size range for the bioactive glass is small and less than 90 microns is recommended. Particle sizes less than 10 microns as well as less than 2 microns can also be used. Particles of such a small size range generally provide for the advantages of the present invention but do not illicit any undesirable immune response.

Topical antibiotics are antibiotic s suitable for skin treatment. Examples of such antibiotics include: chloramphenicol, chiortetracycline, clyndamycin, clioquinol, erythromycin, framycetin, gramicidin, fusidic acid, gentamicin, mafenide, mupiroicin, neomycin, polymyxin B, bacitracin, silver sulfadiazine, tetracycline and chlortetracycline. Those of ordinary skill in the art will appreciate that there are other appropriate topical antibiotics such as those listed in U.S.P.D.

The bioactive glass and topical antibiotic can be combined in any pharmaceutically acceptable carrier to facilitate application to the wound. For example, the composition of the present invention can be combined with an ointment, white petrolatum, mineral oil and others known to those of ordinary skill in the art.

It is also within the scope of the present invention to combine the bioactive glass and topical antibiotic of the present invention with other wound and burn treatments or dressings such as collagen, fibrin, fibronectin, vitamin E, gauze, cotton, cellulosic, synthetic wound or burn dressings and other wound or burn dressings/treatments known to those of ordinary skill in the art. Dressings of fiberglass and fiberglass made from fibers of bioactive glass can also be used.

The present invention is also directed to a method for grafting skin including the application of particulate bioactive glass to the graft before it is placed in its intended location. The graft may also be further treated with a topical antibiotic prior to placement. The application of bioglass to grafts is intended to increase the likelihood that the graft will "take" and incorporate in the host bed.

While not being bound to any particular theory or mechanism, it is believed that the high surface area and reactivity of particulate bioactive glass provides for a release of sodium which increases pH and increase oxygen in the wound or burn which otherwise has a lower pH. This has a bacteriostatic effect and permits the antibiotic to function by activating various growth factors implicated in tissue repair. These reactions cause a higher negative surface charge on the glass surface and the development of a high specific surface area (e.g. from 0.5 $m^2/g$ initially to over 50 $m^2/g$ by 12 hours) which attracts collagen, fibronectin and cells. Moreover, the bioactive glass provides for the precipitation of calcium and phosphorus naturally present in the wound exudate and blood which cause the rapid formation of a calcium and phosphate layer that may incorporate collagen, fibrin and fibronectin to stabilize the wound quickly and effectively. In some cases, wounds or burns healed with the composition or method of the present invention heal without the necessity of scab formation. That is, new epithelial tissue is directly formed.

It has been determined most preferable to mix the particulate bioactive glass and the antibiotic of the present invention just before application to the wound or burn. If the two are mixed well prior to application, e.g. one week, the ability of the composition to accelerate would healing is compromised. It is believed that such early premixing results in a reaction between the organic in the antibiotic and the bioactive glass thereby reducing the effectiveness of the particulate bioactive glass. Accordingly, the present invention is also directed to the incorporation of the bioactive particulate glass and a topical antibiotic in a two part system wherein the bioactive glass and topical antibiotic are mixed and simultaneously applied. For example, a two part mixing syringe with two separate storage chambers and a mixing chamber can be used. Other two part system s could also be used. For example, the particulate bioactive glass can be incorporated into a bandage and the topical antibiotic can be applied to the wound or burn which is followed by application of the bandage. Other two part delivery systems are known to those of ordinary skill in the art.

EXAMPLE I

Figure 2:
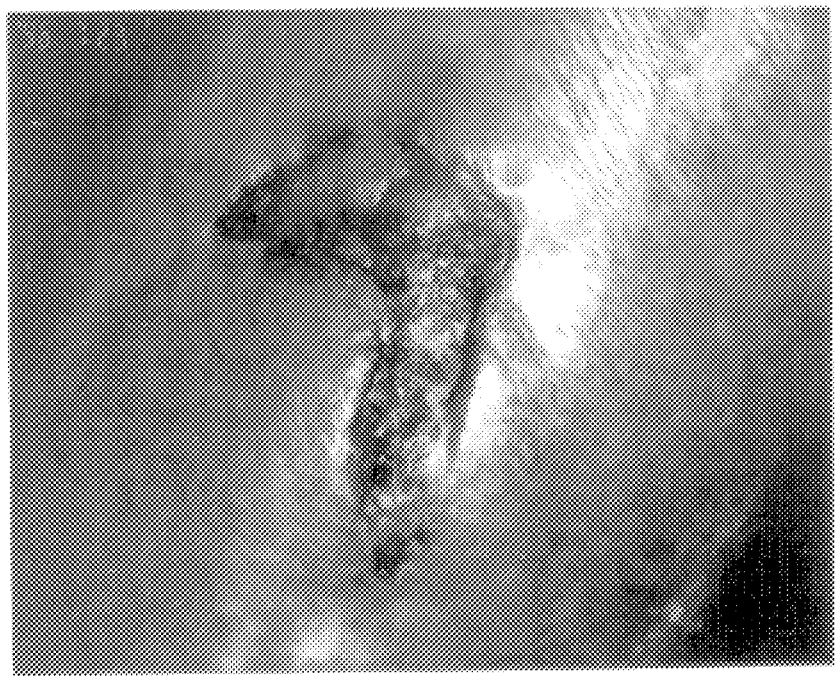
FIG. 2 is a photograph of the same wound of FIG. 1 after treatment with a composition in accordance with the present invention taken 4 days after the photograph of FIG. 1.
Figure 3:
FIG. 3 is a photograph of the same wound of FIG. 2 taken 7 days after the photograph of FIG. 2.
Figure 4:
FIG. 4 is a photograph of the same wound of FIG. 2 taken 7 days after the photograph of FIG. 3.

FIG. 1 is a photograph of a wound in patient with vasculitis taken soon after the wound was inflicted before treatment with a composition in accordance with the present invention. This wound was treated with a mixture of particulate bioactive glass of fine particle size and a topical antibiotic including sulfadiazine. This type of wound would typically require an overall healing time of about 3 months. As depicted in FIGS. 2–4, the healing process is substantially reduced by a composition in accordance with the present invention.

For example, as depicted in FIG. 2, after only 4 days, seepage of the wound is stopped and the surface of the wound appears dry. If one were to apply only a topical antibiotic to such a wound in a patient with vasculitis it would normally take about 2 weeks to stop seepage. In FIG. 3, it is shown that the healing mechanism is well underway and that fatty tissue has covered the surface of the wound after only 11 days. FIG. 4 shows that after only 18 days, the wound is 50% healed. In a patient with vasculitis, it normally takes about 6–8 weeks to reach the 50% healed stage in a wound of the type pictured in the figures.

EXAMPLE II

A diabetic suffering from delayed healing lesions was treated with a mixture of particulate bioactive glass of less than $40\mu$ and an equal volume of NEOSPORIN™. The mixture was applied directly to the delayed healing lesions of about ½ cm by ½ cm. These lesions normally remain non-healing for over 14 days. The mixture was applied twice a day. Within 24 hours seepage ceased. Wound closure and healing was complete within 5 days. Within 48 hours, scar tissue was apparent around the edges of the defect.

What is claimed is:

1. A composition for the healing of wounds and burns comprising particulates of bioactive glass and at least one topical antibiotic, the bioactive glass comprising a composition by weight percentage:

| | |
|---|---|
| $SiO_2$ | 40–60 |
| CaO | 10–30 |
| $Na_2O$ | 10–35 |
| $P_2O_5$ | 2–8 |
| $CaF_2$ | 0–25 |
| $B_2O_3$ | 0–10 |
| $K_2O$ | 0–8 |
| MgO | 0–5 | and a particle size range less than 90 microns.

2. A wound or burn treatment apparatus comprising a topical antibiotic in a first chamber, a non-interconnected particulate bioactive glass in a second chamber and a mixing means for mixing the topical antibiotic and the non-interconnected particulate bioactive glass.

3. The apparatus of claim 2, wherein said wound or burn treatment apparatus is a multi chamber syringe.

4. The composition of claim 1, wherein said bioactive glass has a particle size range less than 10 microns.

5. The composition of claim 1, wherein said bioactive glass has a particle size range less than 2 microns.

6. The composition of claim 1, wherein said topical antibiotic is chloramphenicol, chlortetracycline, clyndamycin, clioquinol, erythromycin, framycetin, gramicidin, fusidic acid, gentamicin, mafenide, mupiroicin, neomycin, polymyxin B, bacitracin, silver sulfadiazine, tetracycline, chlortetracycline, or combinations thereof.

7. The composition of claim 1, further comprising a pharmaceutically acceptable carrier.

8. The composition of claim 7, wherein said pharmaceutically acceptable carrier is an ointment, gel, white petrolatum, light mineral oil, or mixtures thereof.

9. A method for treating wounds and burns comprising contacting a wound with an effective wound healing amount of particulate bioactive glass and topical antibiotic thereby providing for a release of sodium in the wound.

10. A method for grafting skin comprising applying an effective, non-interconnected particulate bioactive glass to a graft of skin and then placing the graft.

11. The method of claim 10, further comprising applying a topical antibiotic to the graft.

12. A method for the healing of wounds or burns comprising contacting a wound or burn with an effective wound or burn healing amount of a particulate bioactive glass thereby providing for a release of sodium in the wound.

* * * * *

UNITED STATES PATENT AND TRADEMARK OFFICE
CERTIFICATE OF CORRECTION

PATENT NO. : 5,834,008

DATED : November 10, 1998

INVENTOR(S) : David C. Greenspan and Jon K. West

It is certified that error appears in the above-identified patent and that said Letters Patent is hereby corrected as shown below:

Column 1, line 32, insert --)-- after reference;

Column 2, line 9, delete "form" and insert therefor --from--;

Column 2, line 29, delete "substance" and insert therefor --substrances--;

Column 2, line 35, between PMN'S and are, insert --,--;

Column 3, line 15, delete "buds" and insert therefor --beds--;

Column 3, line 21, delete "molecule" and insert therefor --molecules--;

Column 3, line 30, delete "--";

Column 3, line 32, delete "peptidasees" and insert therefor --peptidases--;

Column 3, line 57, delete "form" and insert therefor --from--;

Column 3, line 57, delete "crosslink" and insert therefor --crosslinking--;

Column 4, line 8, between limbs and have, insert --,--;

Column 4, line 8, delete "injury" and insert therefor --injuries--;

Column 4, line 22, delete "moisture" and insert therefor --moist--;

Column 5, line 32, delete "antibiotic s" and insert therefor --antibiotics;

Column 5, line 34, delete "chiortetracycline,";

Column 5, line 40, between in and U.S.P.D., insert --the--;

Column 5, line 51, delete "cellulosic" and insert therefor --cellulose--;

Column 5, line 66, delete "increase" and insert therefor --increases--;

UNITED STATES PATENT AND TRADEMARK OFFICE
CERTIFICATE OF CORRECTION

PATENT NO. : 5,834,008

DATED : November 10, 1998

INVENTOR(S) : David C. Greenspan and Jon K. West

It is certified that error appears in the above-identified patent and that said Letters Patent is hereby corrected as shown below:

Column 6, line 5, between e.g. and from insert --,--;

Column 6, line 30, delete "system s" and insert therefor --systems--;

Column 7, line 19, delete "non-interconnected";

Column 7, line 21, delete "non-";

Column 7, line 22, delete "interconnected particulate";

Column 8, line 2, delete "chlortetracycline,";

Column 8, line 18, delete ", non-interconnected" and insert therefor -- amount of a--;

Signed and Sealed this

Twenty-first Day of September, 1999

Attest:

Q. TODD DICKINSON

*Attesting Officer*     *Acting Commissioner of Patents and Trademarks*